United States Patent [19]

Cai et al.

[11] Patent Number: 5,703,093
[45] Date of Patent: Dec. 30, 1997

[54] COMPOUNDS AND METHODS FOR THE TREATMENT OF CARDIOVASCULAR, INFLAMMATORY AND IMMUNE DISORDERS

[75] Inventors: Xiong Cai, Framingham; Aberra Fura, Cambridge; Changgeng Qian, Wayland, all of Mass.

[73] Assignee: Cytomed, Inc., Cambridge, Mass.

[21] Appl. No.: 454,748

[22] Filed: May 31, 1995

[51] Int. Cl.$^6$ .................. A61K 31/34; C07D 307/16
[52] U.S. Cl. .................. 514/312; 514/336; 514/397; 514/428; 514/438; 514/473; 546/283; 548/153; 548/315.7; 548/567; 549/65; 549/77; 549/496
[58] Field of Search .................. 549/496, 65, 77; 546/283; 542/153, 315.7, 567; 514/312, 336, 397, 428, 438, 473

[56] References Cited

U.S. PATENT DOCUMENTS

| | | | |
|---|---|---|---|
| 2,690,988 | 10/1954 | Jones et al. | 167/33 |
| 4,166,452 | 9/1979 | Generales, Jr. | 128/741 |
| 4,256,108 | 3/1981 | Theeuwes | 128/260 |
| 4,265,874 | 5/1981 | Bonsen et al. | 424/15 |
| 4,522,811 | 6/1985 | Eppstein et al. | 514/2 |
| 4,539,332 | 9/1985 | Biftu et al. | 514/461 |
| 4,595,693 | 6/1986 | Biftu et al. | 514/461 |
| 4,604,407 | 8/1986 | Haslanger et al. | 514/575 |
| 4,656,190 | 4/1987 | Shen et al. | 514/529 |
| 4,757,084 | 7/1988 | Biftu et al. | 514/438 |
| 4,841,968 | 6/1989 | Dunn et al. | 128/335.5 |
| 4,845,129 | 7/1989 | Anderson et al. | 514/600 |
| 4,871,756 | 10/1989 | Gillard et al. | 514/381 |
| 4,873,259 | 10/1989 | Summers, Jr. et al. | 514/443 |
| 4,876,346 | 10/1989 | Musser et al. | 546/172 |
| 4,891,363 | 1/1990 | Nakamura et al. | 514/94 |
| 4,910,206 | 3/1990 | Houlihan | 514/292 |
| 4,916,145 | 4/1990 | Tilley et al. | 514/357 |
| 4,959,361 | 9/1990 | Walser | 514/220 |
| 4,987,132 | 1/1991 | Mase et al. | 514/252 |
| 4,992,428 | 2/1991 | Houlihan et al. | 514/63 |
| 4,996,203 | 2/1991 | Biftu et al. | 514/231.5 |
| 5,001,123 | 3/1991 | Biftu et al. | 514/235.2 |
| 5,037,853 | 8/1991 | Brooks et al. | 514/595 |
| 5,047,420 | 9/1991 | Graham et al. | |
| 5,110,831 | 5/1992 | Magolda et al. | 514/645 |
| 5,112,848 | 5/1992 | Brooks et al. | 514/424 |
| 5,169,854 | 12/1992 | Brooks et al. | 514/314 |
| 5,175,183 | 12/1992 | Brooks et al. | 514/438 |
| 5,183,818 | 2/1993 | Brooks et al. | 549/496 |
| 5,187,192 | 2/1993 | Brooks et al. | 514/445 |
| 5,234,950 | 8/1993 | Edwards et al. | 514/473 |
| 5,244,896 | 9/1993 | Borcherding et al. | 514/258 |
| 5,288,751 | 2/1994 | Brooks et al. | 514/438 |
| 5,326,787 | 7/1994 | Brooks et al. | 514/507 |
| 5,334,616 | 8/1994 | Brooks et al. | 514/438 |
| 5,344,843 | 9/1994 | Guthrie et al. | 514/471 |
| 5,358,938 | 10/1994 | Cai et al. | 514/231.5 |
| 5,420,164 | 5/1995 | Mishina et al. | 514/596 |
| 5,434,151 | 7/1995 | Cai et al. | 514/231.5 |
| 5,463,083 | 10/1995 | Biftu et al. | 549/496 |

FOREIGN PATENT DOCUMENTS

| | | | |
|---|---|---|---|
| 0 144 804 | 6/1985 | European Pat. Off. | C07D 307/12 |
| 0 199 324 | 10/1986 | European Pat. Off. | C07D 307/10 |
| 0 217 204 | 4/1987 | European Pat. Off. | C07D 333/16 |
| 0 252 823 A1 | 1/1988 | European Pat. Off. | C07D 513/04 |
| 0 257 921 | 3/1988 | European Pat. Off. | |
| 0 319 947 A2 | 6/1989 | European Pat. Off. | C07C 149/36 |
| 0 322 033 | 6/1989 | European Pat. Off. | C07D 307/12 |
| 0 338 993 A1 | 10/1989 | European Pat. Off. | C07D 495/14 |
| 0 365 089 A2 | 4/1990 | European Pat. Off. | C07D 333/18 |
| 0 367 110 A1 | 5/1990 | European Pat. Off. | C07D 495/22 |
| 0 388 309 A2 | 9/1990 | European Pat. Off. | C07D 513/04 |
| 0 402 150 A1 | 12/1990 | European Pat. Off. | C07D 307/12 |
| 0 402 151 | 12/1990 | European Pat. Off. | C07D 307/12 |
| 0 402 155 | 12/1990 | European Pat. Off. | C07D 405/04 |
| 0 402 156 | 12/1990 | European Pat. Off. | C07D 405/04 |
| 0 416 609 | 3/1991 | European Pat. Off. | C07D 333/58 |
| 0 617 032 | 9/1994 | European Pat. Off. | C07D 401/12 |
| 3701344 | 7/1987 | Germany | C07D 495/14 |
| 3724031 | 1/1988 | Germany | C07D 495/14 |
| 3724164 | 1/1988 | Germany | C07D 487/04 |
| 2197650 | 5/1988 | Germany | C07D 307/10 |
| 3936828 | 5/1990 | Germany | C07D 495/14 |
| 4006471 | 9/1990 | Germany | C07D 495/14 |
| 2233974 | 1/1991 | Germany | C07D 401/12 |
| 2 263 109 | 7/1993 | United Kingdom | C07D 409/04 |
| 0904299 | 5/1989 | WIPO | 549/496 |
| WO 90/12015 | 10/1990 | WIPO | C07D 519/00 |
| WO 91/17157 | 11/1991 | WIPO | C07D 405/12 |
| WO 92/09566 | 6/1992 | WIPO | C07C 273/18 |
| WO 92/13848 | 8/1992 | WIPO | C07D 307/14 |
| WO 92/15294 | 9/1992 | WIPO | A61K 31/34 |
| WO 93/01191 | 1/1993 | WIPO | C07D 471/04 |
| WO 93/16075 | 8/1993 | WIPO | C07D 471/04 |
| WO 94/01430 | 1/1994 | WIPO | C07D 333/18 |
| WO 94/04537 | 3/1994 | WIPO | C07D 495/04 |
| WO 94/06790 | 3/1994 | WIPO | C07D 339/06 |
| WO 95/18610 | 7/1995 | WIPO | A61K 31/34 |
| WO 96/00212 | 1/1996 | WIPO | C07D 207/00 |

OTHER PUBLICATIONS

Backvall, et al., "A Stereocontrolled Organopalladium Route to 2,5-Disubstituted Pyrrolidine Derivatives. Application to the Synthesis of a Venom Alkaloid of the Ant Species *Monomorium latinode*," *J. Org. Chem.*, 55:826–831 (1990).

Bartroli, J., "Design of Potent Linear PAF Antagonists," *J. Med. Chem.*, 34:3328–3334 (1991).

Biftu, T., et al., *Abstr. of 6th Int. Conf. on Prostaglandins and Related Compounds*, Florence, Italy, p. 302 (Jun. 3–6, 1986).

Biftu, T., et al., "Confirmation and Activity of Tetrahydrofuran Lignans and Analogues as Specific Platelet Activating Factor Antagonists," *J. Med. Chem.*, 29(10):1917–1921 (1986).

(List continued on next page.)

*Primary Examiner*—C. Warren Ivy
*Assistant Examiner*—Lyman H. Smith
*Attorney, Agent, or Firm*—Kilpatrick Stockton LLP

[57] ABSTRACT

Tetrahydrofurans, tetrahydrothiophenes, pyrrolidines and cyclopentanes are disclosed that reduce the chemotaxis and respiratory burst leading to the formation of damaging oxygen radicals of polymorphonuclear leukocytes during an inflammatory or immune response. It has been determined that 5-lipoxygenase activity, oral availability, and stability in vivo (for example, glucuronidation rate) can vary significantly among the optical isomers of the disclosed compounds.

22 Claims, 2 Drawing Sheets

OTHER PUBLICATIONS

Bowles, et al., "A Convenient Preparation of Cyclic Ether Acetals Mediated by Trifluoroacetic Anhydride", *Synlett*, pp. 111–112 (1993).

Carlcellar, E., et al., "4–Substituted 2–Alkoxytetrahydrofurans as Potent and Long–Lasting PAF Antagonists," *J. Med. Chem.*, 35(4):676–683 (1992).

Carter, et al., "5–Lipoxygenase Inhibitory Activity of Zileuton," *J. of Pharmacol. and Exp. Thera.*, 256(3);929–937 (1991).

Corey, E.J. et al., "Dual Binding Modes to the Receptor for Platelet Activating Factor (PAF) of Anti–PAF Trans–2, 5–Diarylfurans," *Tetrahedron Letters*, 29(24):2899–2902 (1988).

Crawley, G.C., "Methoxytetrahydropyrans. A New Series of Selective and Orally Potent 5–Lipoxygenase Inhibitors," *J. Med. Chem.*, 35(14):2600–2609 (1992).

Danyoshi et al., "Pyrrolidine Derivatives as Inhibitors of Platelet Aggregation Induced by Platelet Activating Factor," *Chem. Pharm. Bull.*, 37(7):1969–1970 (1989).

Erez, et al., "Narcotic Antagonistic Potency of Bivalent Ligands Which Contain Beta–Naltrexamine. Evidence for Bridging between Proximal Recognition Sites," *J. of Med. Chem.*, 25(7):847–849 (1982).

Feinmark, S.J., "Leukotriene, $C_4$ Biosynthesis During Polymorphonuclear Leukocyte–Vascular Cell Interactions," *Methods in Enzymology*, Murphy and Fitzpatrick, eds., Academic Press, Inc., Harcourt Brace Jovanovich, publishers, New York, NY, vol. 187, pp. 559–560 (1990).

Foye, (Editor) "Bioisosterism," *Principles of Med. Chem.*, Second Edition, pp. 80–81 (Lea & Febiger, Philadelphia, 1981).

Goldstein, et al., "Dual Inhibitors of Platelet Activating Factor and 5–Lipoxygenase. I., 2,40Diaryl–1,3–dithiolanes," *Med. Chem. Res.*, 2:443–450 (1992).

Goldstein, et al., "Dual Inhibitors of Platelet Activating Factor and 5–Lipoxygenase. II. Novel 2,4–Diaryl–1,3–dithiolanes with Iron–Chelating Functionalities," *Med. Chem. Res.*, 2:451–456 (1992).

Graham, D.W., et al., "1,3–Diarylcyclopentanes: A New Class of Potent PAF Receptor Antagonists," 197th ACS National Meeting, Division of Medicinal Chemistry, poster No. 25, Dallas, Texas (Apr. 9–14, 1989).

Guthrie, R.W., et al., "Propenyl Carboxamide Derivatives As Antagonists of Platelet Activating Factor," *J. Med. Chem.*, 33:2856–2864 (1990).

Hwang, S., "Specific Receptors of Platelet–Activating Factor, Receptor Heterogeneity, and Signal Transduction Mechanisms," *J. Lipid Mediators*, 2:123–158 (1990).

Hwang, S., et al., "Trans–2,5–bis–(3,4,5–trimethoxyphenyl)tetrahydrofuran," *Journal of Biological Chemistry*, 260(29):15639–15645 (1985).

Hwang, S., et al., "Biochemical and Pharmacological Charactgerization of L–659, 989: An Extremely Potent, Selective and Competitive Receptor Antagonist of Platelet–Activating Factor," *J. Pharmacol. Ther.*, 246(2):534–541 (1988).

Ikeda et al., "Preparation of Hydroxamic Acid and N–Hydroxyurea Derivatives and Their Use as Lipoxygenase Inhibitors," *Chemical Abstracts*, vol. 118, Abstract No. 59426 (1993).

Lavé, D., et al., "Pyrrolo [1,2–c]Thiazole Derivatives: Potent PAF Receptor Antagonists," *Drugs of the Future*, 14(9):891–898 (1989).

McColl, S.R., "Determination of 5–Lipoxygenase Activity in Human Polymorphonuclear Leukocytes Using High–Performance Liquid Chromatography," *J. Chromatography*, 378:444–449 (1986).

Musser, J.H., et al., "5–Lipoxygenase: Properties, Pharmacology, and the Quinolinyl(bridged)aryl Class of Inhibitors," *J. Med. Chem.*, 35(14):2502–2524 (1992).

O'Donnell, M., et al., "Comparison of the Pulmonary Pharmacoogy of Leukotrienes and PAF: Effects of Their Antagonists," *Therapeutic Approaches to Inflammatory Diseases*, Proceedings of the Fourth International Conference of the Inflammation Research Association, pp. 169–193; White Haven, Pennsylvania (Oct. 23–27, 1988).

Ogiso, A., et al., "The Structure of Futoenone, A Novel Spiro–Cyclohexadienone Derivative," *Tetrahedron Letters*, No. 16, pp. 2003–2008 (1968).

Ogiso, a., et al., "The Structure and Total Synthesis of Futoenone, A Constitute of *Piper futokadzura* SIEB. et ZUCC.¹⁾," *Chem. Pharm. Bull.*, 18(1):105–114 (1970).

Page, C. et al., "PAF: New Antagonists, New Roles in Diseases and a Major Role in Reproductive Biology," *Trends in Pharmacol. Sci.*, pp. 256–257 (1989).

Ponpipom, M.M., et al., "Structure–Actitvity Relationships of Kadsurenone Analogues," *J. Med. Chem.*, 30:136–142 (1987).

Ponpipom, M.M., et al., "(±)–TRANS–2–(3–Methoxy–5–Methylsulfonyl–4–Propoxyphenyl)–5–(3,4,5–Trimethoxyphenyl) Tetrahydrofuran (L–659,989), A Novel, Potent PAF Receptor Antagonist," *Biochemical and Biophysical Research Communications*, 150(3):1213–1220 (1988).

Sahoo, et al., "Synthesis and Biological Activity of MK 287 (L–680,573): A Potent, Specific, and Orally Active PAF Receptor Antagonist," *Bioorg. & Med. Chem. Lett.*, 1(6):327–332 (1991).

Schwenk, et al., "Identification of 5–Oxo–15–hydroxy–6,8,11,13–eicosatetraenoic Acid as a Novel and Potent human Eosinophil Chemotactic Eicosanoid," *J. Biol. Chem.* 267(18):12482–12488 (1992).

Seminaro and Gleich, "The role of eosinophils in the pathogenesis of asthma," *Curr. Opin. in Immunol.*, 6:860–864 (1994).

Shen, T.Y., "Characterization of a Platelet–Activating Factor Receptor Antagonist Isolated from Haifenteng (*Piper futokadsura*): Specific Inhibition of in vitro and in vivo Platelet–Activating Factor–Induced Effects," *Proc. Nat'l. Acad. Sci. USA*, 82:672–676 (1985).

Shen and Hussaini, "Kadsurenone and Other Related Lignans as Antagonists of Platelet–Activating Factor Receptor," *Methods in Enzymol.*, 187:446–454 (1990).

Shizuri, et al., "Synthesis of some physiologically active substances using anodic oxidation of phenols as a key–step," *Tennen Yuki Kagobutsu Toronkai Koen Yoshishu*, *Chem. Abstracts*, Abstract 209491p (1983).

Talapatra, et al., "Maglifloenone, a novel spirocyclohexadienone neolignan and other constituents from Magnolia liliflora," *Chem. Abstracts*, Abstract No. 52493k (1982).

Terashita, et al., "CV–3988—A Specific Antagonist of Platelet Ativating Factor (PAF)," *Life Sciences*, 32(17):1975–1982 (1983).

Weber, K.H., et al., "Hetrazepines as Antagonists of Platelet Activating Factor," *Medicinal Research Reviews*, 9(1):181–218 (Jan.–Mar. 1989).

Wood, et al., "Cyclic Ether Acetal Platelet Activating Factor (PACF) Receptor Antagonists II: Imidazo[4,5–c]Pyridyl Derivatives," *Bioorg. & Med. Chem. Lett.*, 3(8):1499–1504 (1993).

Yeadon, et al., "Effect of BW B70C, a novel inhibitor of arachidonic acid 5–lipoxygenase, on allergen–induced bronchoconstriction and late–phase lung eosinophil accumulation in sensitised guinea–pigs," *Agents and Actions*, 38:8–18 (1993).

Communication dated Mar. 4, 1997 in European Patent App. No. 95907972.4.

COMPOUNDS AND METHODS FOR THE TREATMENT OF CARDIOVASCULAR, INFLAMMATORY AND IMMUNE DISORDERS

FIELD OF THE INVENTION

This invention is in the area of 2,5-disubstituted tetrahydrothiophenes, tetrahydrofurans, pyrrolidines and 1,3-disubstituted cyclopentanes. The compounds exhibit biological activity by inhibiting the enzyme 5-lipoxygenase.

BACKGROUND OF THE INVENTION

Leukotrienes are potent local mediators, playing a major role in inflammatory and allergic responses, including arthritis, asthma, psoriasis, and thrombotic disease. Leukotrienes are straight chain eicosanoids produced by the oxidation of arachidonic acid by lipoxygenases. Arachidonic acid is oxidized by 5-lipoxygenase to the hydroperoxide 5-hydroperoxy-eicosatetraenoic acid (5-HPETE), that is converted to leukotriene $A_4$, that in turn can be converted to leukotriene $B_4$, $C_4$, or $D_4$. The slow-reacting substance of anaphylaxis is now known to be a mixture of leukotrienes $C_4$, $D_4$, and $E_4$, all of which are potent bronchoconstrictors. There has been a research effort to develop specific receptor antagonists or inhibitors of leukotriene biosynthesis, to prevent or minimize pathogenic inflammatory responses mediated by these compounds.

European Patent Application Nos. 90117171.0 and 901170171.0 disclose indole, benzofuran, and benzothiophene lipoxygenase inhibiting compounds.

Recently, it was reported that the tetrahydrothiophene derivative of L-652,731, trans-2,5-bis-(3,4,5-trimethoxyphenyl)tetrahydrothiophene (L-653,150), is a potent PAF antagonist and a moderate inhibitor of 5-lipoxygenase. It has been disclosed that certain 2,5-diaryl tetrahydrothiophenes are PAF antagonists and leukotriene synthesis inhibitors. (Biftu, et al., *Abstr. of 6th Int. Conf. on Prostaglandins and Related Compounds*, Jun. 3–6, 1986, Florence, Italy; U.S. Pat. No. 4,757,084 to Biftu); WO 92/15294; WO 94/01430; WO 94/04537; and WO 94/06790.

WO 92/13848 discloses a class of racemic lipoxygenase-inhibiting hydroxamic acid and N-hydroxyurea derivatives of the structure wherein $R^1$ is hydrogen, alkyl, alkenyl, amino or substituted amino, $R^4$ is hydrogen, a pharmaceutically acceptable cation, aroyl or alkoyl, A is alkylene or alkenylene, X is oxygen or sulfur, each Y is hydrogen, halo, cyano, hydroxy, alkyl, alkoxy, alkylthio, alkenyl, alkoxyalkyl, cycloalkyl, aryl, aryloxy, arylalkyl, arylalkenyl, arylalkoxy or substituted aryl, Z is oxygen or sulfur, m is 0 or 1, n is 1 to 5 and p is 2 to 6, inhibit the enzyme lipoxygenase.

Given the significant number of pathological immune and inflammatory responses that are mediated by 5-lipoxygenase, there remains a need to identify new compounds and compositions that inhibit this enzyme.

Therefore, it is an object of the present invention to provide compounds that reduce the chemotaxis and respiratory burst leading to the formation of damaging oxygen radicals during an inflammatory or immune response.

It is another object of the present invention to provide pharmaceutical compositions for the treatment of pathological immune or inflammatory disorders mediated by 5-lipoxygenase.

It is another object of the present invention to provide a method for the treatment of pathological immune or inflammatory disorders mediated by products of 5-lipoxygenase.

SUMMARY OF THE INVENTION

Compounds of Formula I are provided wherein:

Ar is an aryl or heteroaryl group that is optionally substituted, preferably with halo (including but not limited to fluoro), lower alkoxy (including methoxy), lower aryloxy (including phenoxy), W, cyano, or $R^3$;

m is 0 or 1;

n is 1–6;

W is independently —AN(OM)C(O)N($R^3$)$R^4$, —N(OM)C(O)N($R^3$)$R^4$, —AN($R^3$)C(O)N(OM)$R^4$, —N($R^3$)C(O)N(OM)$R^4$ —AN(OM)C(O)$R^4$, —N(OM)C(O)$R^4$—, AC(O)N(OM)$R^4$, —C(O)N(OM)$R^4$, or —C(O)NHA; A is lower alkyl, lower alkenyl, lower alkynyl, alkylaryl or arylalkyl groups, wherein one or more carbons optionally can be replaced by O, N, or S (with valence completed with hydrogen or oxygen as necessary), however, —Y—A—, —A—, or —AW— should not include two adjacent heteroatoms (i.e., —O—O—, —S—S—, —O—S—, etc.) (In one embodiment, lower alkyl is a branched alkyl group such as —(CH$_2$)$_n$C(alkyl)H—, wherein n is 1–5, and specifically —(CH$_2$)$_2$C(CH$_3$)H—, or lower alkynyl of the formula C≡C—CH(alkyl)—, including —C≡C—CH(CH$_3$)—);

M is hydrogen, a pharmaceutically acceptable cation, or a metabolically cleavable leaving group;

X is O, S, S(O), S(O)$_2$, NR$^3$, or CHR$^5$;

Y is O, s, S(O), S(O)$_2$, NR$^3$, or CHR$^5$;

Z is O, S, S(O), S(O)$_2$, NR$^3$;

$R^1$ and $R^2$ are independently hydrogen, lower alkyl including methyl, cyclopropylmethyl, ethyl, isopropyl, butyl, pentyl hexyl, and $C_{3-8}$ cycloalkyl, for example, cyclopentyl; halo lower alkyl, for example, trifluoromethyl; halo, for example fluoro; and —COOH;

$R^3$ and $R^4$ are independently hydrogen or alkyl, alkenyl, alkynyl, aryl, arylalkyl, alkylaryl, $C_{1-6}$ alkoxy-$C_{1-10}$ alkyl, $C_{1-6}$ alkylthio-$C_{1-10}$ alkyl, heteroaryl, or heteroarylalkyl-;

$R^5$ is hydrogen, lower alkyl, lower alkenyl, lower alkynyl, arylalkyl, alkyaryl, —AN(OM)C(O)N($R^3$)$R^4$, —AN($R^3$)C(O)N(OM)$R^4$, —AN(OM)C(O)$R^4$, —AC(O)N (OM)$R^4$, —AS(O)$_x$$R^3$, AS(O)xCH$_2$C(O)$R^3$ AS(O)xCH$_2$CH(OH)$R^3$, or —AC(O)NHR$^3$, wherein x is 0–2;

The Ar group, in one embodiment, is selected from the group consisting of phenyl, trimethoryphenyl, dimethoxyphenyl, fluorophenyl (specifically 4-fluorophenyl), difluorophenyl, pyridyl, dimethoxypyridyl, quinolinyl, furyl, imidazolyl, and thienyl groups.

Nonlimiting examples of preferred compounds are:

wherein $R^{10}$ is halogen, —CN, hydrogen, lower alkyl, lower alkenyl, lower alkynyl, lower alkoxy, or lower aryloxy.

These compounds in general reduce the chemotaxis and respiratory burst leading to the formation of damaging oxygen radicals of polymorphonuclear leukocytes during an inflammatory or immune response. The compounds exhibit this biological activity by inhibiting the enzyme 5-lipoxygenase.

Another embodiment of the present invention is a pharmaceutical composition that includes an effective amount of a compound of Formula I or its pharmaceutically acceptable salt or derivative in combination with a pharmaceutically acceptable carrier for any of the disorders described herein.

A method to treat disorders mediated by 5-lipoxygenase is also disclosed, that includes administering an effective amount of one or more of the above-identified compounds or a pharmaceutically acceptable salt or derivative thereof, optionally in a pharmaceutically acceptable carrier.

It has been surprisingly determined that 5-lipoxygenase activity, oral availability, and stability in vivo (for example, glucuronidation rate) can vary significantly among the optical isomers of the disclosed compounds. Therefore, in one embodiment of the invention, the compound is administered in an enantiomerically enriched form, i.e., substantially in the form of one isomer.

Examples of immune, allergic and cardiovascular disorders include general inflammation, cardiovascular disorders including hypertension, skeletal-muscular disorders, osteoarthritis, gout, asthma, lung edema, adult respiratory distress syndrome, pain, aggregation of platelets, shock, rheumatoid arthritis, juvenile rheumatoid arthritis, psoriatic arthritis, psoriasis, autoimmune uveitis, allergic encephalomyelitis, systemic lupus erythematosis, acute necrotizing hemorrhagic encephalopathy, idiopathic thrombocytopenia, polychondritis, chronic active hepatitis, idiopathic sprue, Crohn's disease, Graves ophthalmopathy, primary biliary cirrhosis, uveitis posterior, interstitial lung fibrosis; allergic asthma; and inappropriate allergic responses to environmental stimuli such as poison ivy, pollen, insect stings and certain foods, including atopic dermatitis and contact dermatitis.

The compounds disclosed herein can also be used as research tools to study biological pathways involving leukotrienes.

The following are nonlimiting examples of compounds that fall within Formula I. These examples are merely exemplary, and are not intended to limit the scope of the invention.

trans-2-(3,4,5-trimethoxyphenoxymethyl)-5-[4-N'-methyl-N'-hydroxyureidyl) butyl]tetrahydrofuran trans-2-(3,4,5-trimethoryphenoxymethyl)-5-[4-N'-methyl-N'-hydroxyureidyl)but-1-ynyl]tetrahydrofuran trans-2-(4-fluorophenoxymethyl)-5-[4-N'-methyl-N'-hydroxyureidyl)butyl]tetrahydrofuran trans-2-(4-fluorophenoxymethyl)-5-[4-N'-methyl-N'-hydroxyureidyl) but-1-ynyl]tetrahydrofuran trans-2-(4-fluorophenoxymethyl)-5-[4-N'-butyl-N'-hydroxyureidyl)butyl] tetrahydrofuran trans-2-(4-fluorophenoxymethyl)-5-[4-N'-butyl-N'-hydroxyureidyl)but-1-ynyl]tetrahydrofuran trans-2-(3,4,5-trimethoxyphenoxymethyl)-5-[4-N'-methyl-N-hydroxyureidyl)butyl]tetrahydrofuran trans-2-(3,4,5-trimethoxyphenoxymethyl)-5-[4-N'-methyl-N-hydroxyureidyl)but-1-ynyl]tetrahydrofuran trans-2-(4-fluorophenoxymethyl)-5-[4-N'-methyl-N-hydroxyureidyl)butyl]tetrahydrofuran trans-2-(4-fluorophenoxymethyl)-5-[4-N'-methyl-N-hydroxyureidyl)but-1-ynyl]tetrahydrofuran trans-2-(4-fluorophenoxymethyl)-5-[4-N'-butyl-N-hydroxyureidyl)butyl]tetrahydrofuran trans-2-(4-fluorophenoxymethyl)-5-[4-N'-butyl-N-hydroxyureidyl)but-1-ynyl]tetrahydrofuran trans-2-(3,4,5-trimethoxyphenoxymethyl)-5-[4-N'-methyl-N'-hydroxyureidyl)butyl]tetrahydrothiophene trans-2-(3,4,5-trimethoxyphenoxymethyl)-5-[4-N'-methyl-N'-hydroxyureidyl)but-1-ynyl] tetrahydrothiophene trans-2-(4-fluorophenoxymethyl)-5-[4-N'-methyl-N'-hydroxyureidyl)butyl]tetrahydrothiophene trans-2-(4-fluorophenoxymethyl)-5-[4-N'-methyl-N'-hydroxyureidyl)but-1-ynyl]tetrahydrothiophene trans-2-(4-fluorophenoxymethyl)-5-[4-N'-butyl-N'-hydroxyureidyl)butyl]tetrahydrothiophene trans-2-(4-fluorophenoxymethyl)-5-[4-N'-butyl-N'-hydroxyureidyl)but-1-ynyl]tetrahydrothiophene trans-2-(3,4,5-trimethoxyphenoxymethyl)-5-[4-N'-methyl-N-hydroxyureidyl)butyl]tetrahydrothiophene trans-2-(3,4,5-trimethoxyphenoxymethyl)-5-[4-N'-methyl-N-hydroxyureidyl)but-1-ynyl] tetrahydrothiophene trans-2-(4-fluorophenoxymethyl)-5-[4-N'-methyl-N-hydroxyureidyl)butyl]tetrahydrothiophene trans-2-(4-fluorophenoxymethyl)-5-[4-N'-methyl-N-hydroxyureidyl)but-1-ynyl]tetrahydrofuran trans-2-(4-fluorophenoxymethyl)-5-[4-N'-butyl-N-hydroxyureidyl)butyl]tetrahydrothiophene trans-2-(4-fluorophenoxymethyl)-5-[4-N'-butyl-N-hydroxyureidyl)but-1-ynyl]tetrahydrothiophene Further nonlimiting examples of other compounds that fall within Formula I are set forth below in Table 1.

TABLE 1

DETAILED DESCRIPTION OF THE INVENTION

I. Description and Synthesis of the Compounds
A. Compounds

As used herein, the term "enantiomerically enriched" refers to a compound in the form of at least approximately 95%, and preferably approximately 97%, 98%, 99%, or 100% of a single enantiomer of that compound.

The term alkyl, as used herein, unless otherwise specified, refers to a saturated straight, branched, or cyclic hydrocarbon of $C_1$ to $C_{10}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The alkyl group can be optionally substituted with any appropriate group, including but not limited to $R^3$ or one or more moieties selected from the group consisting of halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term halo, as used herein, refers to chloro, fluoro, iodo, or bromo.

The term lower alkyl, as used herein, and unless otherwise specified, refers to a $C_1$ to $C_6$ saturated straight, branched, or cyclic (in the case of $C_{5-6}$) hydrocarbon, and specifically includes methyl, ethyl, propyl, isopropyl, butyl, isobutyl, t-butyl, pentyl, cyclopentyl, isopentyl, neopentyl, hexol, isohexyl, cyclohexyl, 3-methylpentyl, 2,2-dimethylbutyl, and 2,3-dimethylbutyl, optionally substituted as described above for the alkyl groups.

The term alkenyl, as referred to herein, and unless otherwise specified, refers to a straight, branched, or cyclic (in the case of $C_{5-6}$) hydrocarbon of $C_2$ to $C_{10}$ with at least one double bond, optionally substituted as described above.

The term lower alkenyl, as referred to herein, and unless otherwise specified, refers to an alkenyl group of $C_2$ to $C_6$, and specifically includes vinyl and allyl.

The term lower alkylamino refers to an amino group than has one or two lower alkyl substituents.

The term alkynyl, as referred to herein, and unless otherwise specified, refers to a $C_2$ to $C_{10}$ straight or branched hydrocarbon with at least one triple bond, optionally substituted as described above. The term lower alkynyl, as referred to herein, and unless otherwise specified, refers to a $C_2$ to $C_6$ alkynyl group, specifically including acetylenyl, propynyl, and —C≡C—CH(alkyl)—, including —C≡C—CH($C_3$)—.

The term aryl, as used herein, and unless otherwise specified, refers to phenyl, biphenyl, or napthyl, and preferably phenyl. The aryl group can be optionally substituted with any suitable group, including but not limited to one or more moieties selected from the group consisting of halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, and preferably with halo (including but not limited to fluoro), lower alkoxy (including methoxy), lower aryloxy (including phenoxy), W, cyano, or $R^3$.

The term haloalkyl, haloalkenyl, or haloalkynyl refers to alkyl, alkenyl, or alkynyl group in which at least one of the hydrogens in the group has been replaced with a halogen atom.

The term heteroaryl, heterocycle or heteroaromatic, as used herein, refers to an aromatic moiety that includes at least one sulfur, oxygen, or nitrogen in the aromatic ring, which can optionally be substituted as described above for the aryl groups. Non-limiting examples are pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl, and isoxazolyl.

The term arylalkyl refers to an aryl group with an alkyl substituent.

The term alkylaryl refers to an alkyl group that has an aryl substituent.

The term organic or inorganic anion refers to an organic or inorganic moiety that carries a negative charge and can be used as the negative portion of a salt.

The term "pharmaceutically acceptable cation" refers to an organic or inorganic moiety that carries a positive charge and that can be administered in association with a pharmaceutical agent, for example, as a countercation in a salt. Pharmaceutically acceptable cations are known to those of skill in the art, and include but are not limited to sodium, potassium, and quaternary amine.

The term "metabolically cleavable leaving group" refers to a moiety that can be cleaved in vivo from the molecule to which it is attached, and includes but is not limited to an organic or inorganic anion, a pharmaceutically acceptable cation, acyl (for example (alkyl)C(O), including acetyl, propionyl, and butyryl), alkyl, phosphate, sulfate and sulfonate.

The term 5-lipoxygenase inhibitor refers to a compound that inhibits the enzyme at 30 µM or lower in a broken cell system.

The term pharmaceutically active derivative refers to any compound that upon administration to the recipient, is capable of providing directly or indirectly, the compounds disclosed herein.

The 2,5-disubstituted tetrahydrothiophenes, tetrahydrofurans and pyrrolidines, as well as the 1,3-disubstituted cyclopentanes described herein inhibit the enzyme 5-lipoxygenase and are thus useful in the treatment of humans who have immune allergic or cardiovascular disorders that are mediated by 5-lipoxygenase.

B. Stereochemistry

It has been surprisingly determined that 5-lipoxygenase activity, oral availability, and stability in vivo (for example, glucuronidation rate) can vary significantly among the optical isomers of the disclosed compounds. Therefore, in a preferred embodiment, the active compound or its precursor is administered in an enantiomerically enriched form, i.e., substantially in the form of one isomer. The preferred enantiomer is easily determined by evaluating the various possible enantiomers in selected biological assays, for example, those described in detail herein.

The 2,5-disubstituted tetrahydrofurans, tetrahydrothiophenes, and pyrrolidines exhibit a number of stereochemical configurations. Carbon atoms 2 and 5 in the center ring are chiral, and thus the center ring exists at a minimum as a diastereomeric pair. Each diastereomer exists as a set of enantiomers. Therefore, based on the chiral $C_2$ and $C_5$ atoms alone, the compound is a mixture of four enantiomers.

If non-hydrogen substituents are located on carbon atoms 3 and 4 in the center ring, then the $C_3$ and $C_4$ atoms are also chiral, and can also exist as a diastereomeric pair, that is also a mixture of four enantiomers.

The 1,3-cyclopentanes disclosed herein also exhibit a number of stereochemical configurations. Carbon atoms 1 and 3 in the center ring are chiral, and thus the center ring exists at a minimum as a diastereomeric pair. Each diastereomer exists as a set of enantiomers. Therefore, based on the chiral $C_1$ and $C_3$ atoms alone, the compound is a mixture of four enantiomers.

If non-hydrogen substituents are located on carbon atoms 4 and 5 in the center ring, then the $C_4$ and $C_5$ atoms are also chiral, and can also exist as a diastereomeric pair, that is also a mixture of four enantiomers.

One of ordinary skill in the art can easily synthesize and separate the enantiomers of the disclosed compounds using chiral reagents and known procedures, and can evaluate the biological activity of the isolated enantiomer using methods disclosed herein or otherwise known. Through the use of chiral NMR shift reagents, polarimetry, or chiral HPLC, the optical enrichment of the compound can be determined.

Classical methods of resolution include a variety of physical and chemical techniques. For example, if the compound is basic, one can use chiral acids that form diastereomeric derivatives that may possess significantly different solubility properties. Non-limiting examples of chiral acids include malic acid, mandelic acid, dibenzoyl tartaric acid, 3-bromocamphor-8-sulfonic acid, 10-camphorsulfonic acid, and di-p-toluoyltartaric acid. Similarly, acylation of a free hydroxyl group with a chiral acid also results in the formation of diastereomeric derivatives whose physical properties may differ sufficiently to permit separation.

Enantiomerically pure or enriched compounds can also be obtained by passing the racemic mixture through a chromatographic column that has been designed for chiral separations, or by enzymatic resolution of appropriately modified substrates.

C. Syntheses of Active Compounds

The 2,5-disubstituted tetrahydrofurans, tetrahydrothiophenes, and pyrrolidines disclosed herein can be prepared in a variety of ways known to those skilled in the art, including by methods disclosed by, or routine modifications of the methods disclosed by, Whittaker et al, Synlett, 1993 pp 111, Biorg. Med. Lett., 1993 pp 1499; Achiwa et al., Chem. Pharm. Bull., 1989, pp. 1969. These compounds can be prepared in both racemic and enantiomerically enriched forms.

1,3-Disubstituted cyclopentanes can be prepared using the procedure of Graham, et al. (1.3-Diaryl Cyclopentanes: A New Class of Potent PAF Receptor Antagonists. 197th ACS National Meeting, Dallas, Tex., Apr. 9–14, 1989, Division of Medicinal Chemistry, poster no. 25 (abstract)), or by other known methods.

A general procedure for preparing a hydroxyurea is shown below in Scheme 1.

Scheme 1
Preparation of Hydroxyureas

General procedures for preparing reverse hydroxyureas are shown in Scheme 2.

Scheme 2
Preparation of Reverse Hydroxyureas

-continued
Scheme 2
Preparation of Reverse Hydroxyureas

A general procedure for preparing a hydroxamic acid is shown in Scheme 3.

Scheme 3
Preparation of Hydroxamic Acids

A general procedure for preparing a reverse hydroxamic acid is shown in Scheme 4.

Scheme 4
Preparation of Reverse Hydroxamic Acids

Figure 1:
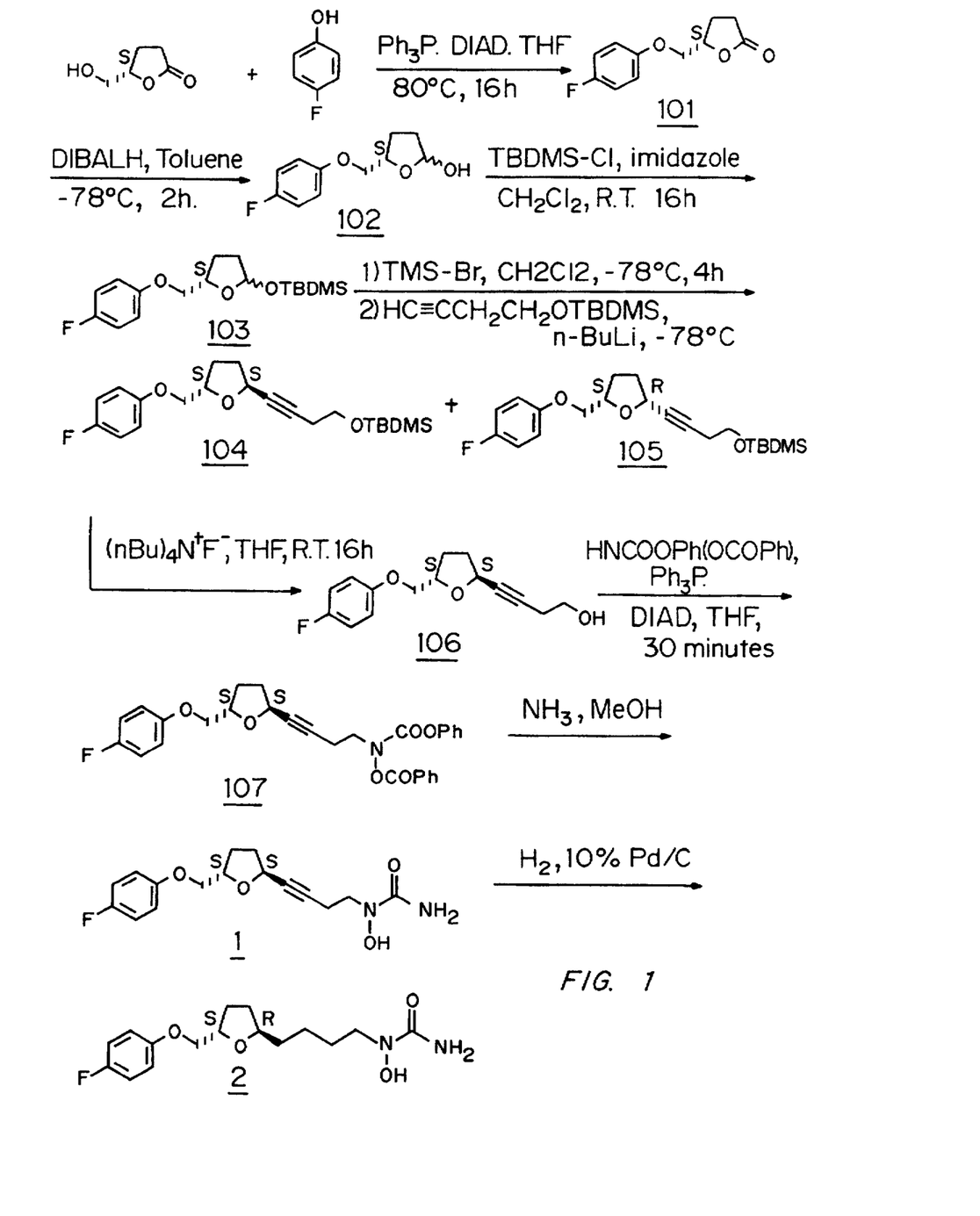
FIG. 1 is an illustration of one process for the synthesis of 2S,5S-trans-2-(4-fluorophenoxymethyl)-5-(4-N-hydroxynreidyl-1-butynyl)tetrahydrofuran (compound 1) and 2S,5R-trans-2-(4-fluorophenoxymethyl)-5-(4-N-hydroxyureidylbutyl) tetrahydrofuran (compound 2).

The following working examples, depicted in FIG. 1, are merely illustrative, and are not intended to limit the scope of the invention. Other compounds falling within the disclosed formula can be prepared by one of skill in the art by modification of the scheme below or by other known methods.

EXAMPLE 1

Preparation of 2S, 5S-trans-2-(4-fluorophenoxymethyl)-5-(4-N-hydroxyureidyl-1-butynyl) tetrahydrofuran (compound 1, FIG. 1) and 2S,5R-trans-2-(4-fluorophenoxymethyl)-5-(4-N-hydroxyureidylbutyl) tetrahydrofuran (compound 2, FIG. 1)

Preparation of 4S-(4-fluorophenoxymethyl)-gammabutyrolactone (compound 101, FIG. 1) To a stirred THF (10 mL) solution of (S)-gamma-butyrolactone (1.0 g, 8.61 mmol), 4-fluorophenol (1.16 g, 10.35 mmol), and triphenylphosphine (2.49 g, 9.49 mmol) was added diisopropoxyl azodicarboxylate (1.87 µL, 9.46 mmol) dropwise. After addition, the reaction mixture was stirred at 80° C. for 16 hours. The solvent was removed and the product was separated by flash column chromatography (silica, 2:1 hexane/ethyl acetate) (1.38 g, 76.3%). $^1$H NMR (CDCl$_3$); 2.27(m, 1H); 2.42(m, 1H); 2.60(m, 1H); 4.04(m, 1H); 4.15(m, 1H); 4.85(m, 1H); 6.84(m, 2H); 6.98(m, 2H).

Preparation of 2S-(4-fluorophenoxymethyl)-5-hydroxytetrahydrofuran (compound 102, FIG. 1). To a stirred solution of lactone 101 (1.38 g, 27.22 mmol) in dry toluene (24 mL) at −78° C. was added a 1.5M toluene solution of DIBAL (6.76 mL, 10.13 mmol) dropwise. The reaction mixture was stirred at −78° C. for 2 hours. The reaction was quenched through the addition of methanol (1.7 ml) while maintaining a temperature of <−60° C. The mixture was warmed to −20° C. followed by the addition of saturated aqueous potassium sodium tartrate solution (10 mL) while maintaining the reaction temperature between −10° and 0° C. The reaction mixture was stirred at room temperature overnight and then the two phases were separated. The aqueous layer was extracted with ethyl acetate. The combined organic layers were washed with water, saturated NaCl solution, and then concentrated in vacuo to leave an oil which was purified by flash column chromatography (silica, 1:1 hexane/ethyl acetate) (1.41 g, 101%). $^1$H NMR (CDCl$_3$); 1.80(m, 1H); 2.05(m, 2H); 2.26(m, 1H); 3.93(m, 2H); 4.04(m, 2H); 4.47(m, 0.5H); 4.61(m, 0.5H); 5.57(m, 0.5H); 5.66(m, 0.5H); 6.88(m, 2H); 6.98(m, 2H).

Preparation of 2S-(4-fluorophenoxymethyl)-5-(t-butyldimethysiloxy) tetrahydrofuran (compounds 103, FIG. 1) To a stirred solution of lactol 102 (1.41 g, 6.65 mmol) in methylene chloride (25 mL) was added imidazole (498.1 mg, 7.32 mmol) and TBDMS chloride (1.10 g, 7.32 mmol). The reaction mixture was stirred at room temperature overnight and then the reaction was filtered and the filtrate was concentrated. The crude product was purified by flash column chromatography using 9:1 hexane/ethyl acetate as a solvent to give a colorless oil which is a mixture of two diasteriomers (ca. 2:1) (1.22 g, 56.2%). $^1$H NMR (CDCl$_3$); 0.11(s, 6H); 0.90(s, 9H); 1.80–2.10(m, 3H); 2.22(m, 1H); 3.91(m, 2H); 4.38(m, 0.33H); 4.50(m, 0.67H); 5.52(m, 0.33H); 5.59(m, 0.67H); 6.86(m, 2H); 6.96(m. 2H).

Preparation of 2S,5S-trans-2-(4-fluorophenoxymethyl)-5-(4-t-butyldimethysiloxy-1-butynyl)tetrahydrofuran (compounds 104, FIG. 1) and 2S, 5R-cis-2-(4-fluorophenoxymethyl)-5-(4-t-butyldimethysiloxy-1-butynyl) tetrahydrofuran (compounds 105, FIG. 1) To a stirred solution of 103 (720 mg, 2.21 mmol) in dry methylene chloride (10 mL), cooled to −78° C. was added TMS bromide (349.8 µL, 2.65 mmol). The reaction mixture was stirred at −78° C. for 4 hours. In a separate flask containing 4-t-butyldimethylsiloxy-1-butyne (812.8 mg, 4.42 mmol) and THF (10 mL) was added n-butyllithium (2.5M in hexane, 2.65 mL, 6.63 mmol). After 30 minutes, this was transferred by cannula to the solution from above. After two hours, the reaction was quenched through the addition of saturated aq. ammonium chloride solution and extracted with methylene chloride, dried over MgSO4, filtered and concentrated. Flash column chromatography (silica, 95:5 hexane/ethyl acetate) yielded two products, trans compound 104 (210 mg) and cis compound 105 (160 mg), and the mixture of these two compounds (50 mg). The total yield is 48.5%. $^1$H NMR (CDCl$_3$); 104: 0.10(s, 6H); 0.91(s, 9H); 1.87(m, 1H); 2.01(m, 1H); 2.22(m, 2H); 2.43(t, 2H); 3.72(t, 2H); 3.92 (d, 2H); 4.47(m, 1H); 4.73(m. 1H); 6.86 (m, 2H); 6.95(t, 2H). 105: 0.09 (s, 6H); 0.90(s, 9H); 1.92–2.20(m, 4H); 2.42 (m, 2H); 3.70(t, 2H); 3.92(m, 1H); 4.07(m, 1H); 4.29(m, 1H); 4.62(m, 1H); 6.86(m, 2H); 6.96(t. 2H.

In the preparation of compounds 104 and 105, oxygen protecting groups known to those skilled in the art other than 4-t-butyldimethysilyl can be used as desired.

In order to determine the stereochemistry of this molecule, a NOE difference experiment was carried out for both 104 and 105. In the NOE difference experiment of 104, the multiplet at 4.73 ppm was irradiated with a very low rf decoupling pulse and the data work-up was done so as to only measure the presence of an increase in signal. This would represent a positive NOE effect and would indicate the close spacial relationship of these protons. In this experiment, a NOE was found for the multiplet at 2.22 ppm which are furan ring protons. When the multiplet at 4.47 ppm was irradiated with a very low rf decoupling pulse and the data work-up was done so as to only measure the presence of an increased in signal. A NOE was found for the multipier at 2.22 ppm which are furan ring protons. Another NOE was also seen for the protons at 3.92 ppm which are the protons on the methylene next to this multiplet, indicating that this multiplet represents the proton next to the methylene.

In the NOE difference experiment of 105, the triplet at 4.62 ppm was irradiated with a very low rf decoupling pulse and the data work-up was done so as to only measure the presence of an increase in signal. This would represent a positive NOE effect and would indicate the close spacial relationship of these protons. In this experiment, a NOE was found for the multiplet at 4.29 ppm which is the other methine furan proton. Another NOE was also seen for the multipier at 2.17 ppm which are furan protons. When the multipier at 4.29 ppm was irradiated with a very low rf decoupling pulse and the data work-up was done so as to only measure the presence of an increase in signal. A NOE was found for the triplet at 4.62 ppm which is the other methine furan proton. Another NOE was seen for the protons at 3.92 and 4.07 ppm which are the protons on the methylene next to this multiplet, indicating that this multipier represents the proton next to the methylene. Another NOE was also seen for the multiplet at 2.11 ppm which are furan protons.

Preparation of 2S,5S-trans-2-(4-flugrophenoxymethyl)-5-(4-t-hydroxy-1-butyl)tetrahydrofuran (compounds 106, FIG. 1)

To a stirred solution of 104 (210 mg, 0.54 mmol) in THF (1.4 mL), cooled in an ice bath, was added tetrabutyl ammonium fluoride (420.3 mg, 1.61 mmol). The ice bath was removed and the reaction was stirred at room temperature for 1 hour. The solvent was removed and the product was separated by flash column chromatography (silica, 1:1 hexane/ethyl acetate) (124 mg, 83.2%). $^1$H NMR (CDCl$_3$); 1.88(m, 1H); 2.02(m, 1H); 2.25(m, 2H); 2.50(m, 2H); 3.72(t, 2H); 3.93(d, 2H); 4.48(m, 1H); 4.76(m, 1H); 6.84(m, 2H); 6.96(t,2H).

Preparation of 2S,5S-trans-2-(4-fluorophenoxymethyl)-5-(4-N,O-bisphenoxycarbonylhydroxylamino-1-butynyl) tetrahydrofuran (compound 107, FIG. 1) To a cooled (ice bath) solution compound 106 (124.0 mg, 0.45 mmol), triphenylphosphine (128.9 mg., 0.49 mmol) and N,O-bisphenoxycarbonyl hydroxylamine (147.3 mg, 0.54 mmol) in THF (5 mL) was added diisopropoxylazodicarboxylate (94.1 µL, 0.48 mmol). The ice bath was removed and the reaction was warmed to room temperature and stirred at room temperature for 30 minutes. The solvent was removed and the product was purified by flash column chromatography (silica, 4:1 hexane/ethyl acetate) (195 mg, 82.0%). $^1$H NMR (CDCl$_3$); 1.85(m, 1H); 2.03 (m, 1H); 2.22(m, 2H); 2.75(m, 2H); 3.92(d, 2H); 4.05(m, 2H); 4.47(m, 1H); 4.76(m, 1H); 6.84(m, 2H); 6.95(m, 2H); 7.26(m, 5H); 7.41(m, 5H).

Preparation of 2S,5S-trans-2-(4-fluorophenoxymethyl)-5-(4-N-hydroxyureidyl-1-butynyl)tetrahydrofuran (compound 1, FIG. 1)

In a screw top vessel was placed $NH_3$ at $-78°$ C. (approximately 1–2 mL). Compound 107 (195.0 mg, 0.37 mmol), predissolved in 20 mL methanol, was added to this cold liquid nitrogen. The vessel was sealed and the dry ice bath was removed. The reaction mixture was stirred at room temperature for 16 hours. The reaction mixture was cooled again by dry ice bath and the pressure was released. The vessel was opened and the solvent was removed. The product was isolated by flash column chromatography using ethyl acetate as a solvent to provide a solid (108 mg, 91.7%). $^1$H NMR (CDCl$_3$); 1.84(m, 1H); 2.01(m, 1H); 2.22(m, 2H); 2.55(t, 2H); 3.75(t, 2H); 3.94(m, 2H); 4.48(m, 1H); 4.74(t, 1H); 5.25(bs, 2H); 6.86(m,2H); 6.98(m, 2H).

Preparation of 2S,5R-trans-2-(4-fluorophenoxymethyl)-5-(4-N-hydroxyureidyl-1-butynyl)tetrahydrofuran (2)

Compound 1 (75 mg, 0.23 mmol) was dissolved in 2 mL of ethyl acetate and then Pd/C (10%) (15 mg) was added and hydrogenated at balloon pressure for 16 hours. The reaction was filtered and the filtrate was concentrated. The product was isolated by flash column chromatography using ethyl acetate as solvent (70 mg, 92.2%). $^1$H NMR (CDCl$_3$); 1.50–1.70(m, 8H); 2.10(m, 2H); 3.58(m, 2H); 3.91(m, 2H); 4.08(m, 1H); 4.40(m, 1H); 5.15(bs, 2H); 6.87(m, 2H); 6.97(t, 2H); 7.40(bs,1H).

II. Pharmaceutical Compositions

Humans, equines, canines, bovines and other animals, and in particular, mammals, suffering from inflammatory diseases, and in particular, disorders mediated by 5-lipoxygenase, can be treated by administering to the patient an effective amount of one or more of the above-identified compounds or a pharmaceutically acceptable derivative or salt thereof in a pharmaceutically acceptable carrier or diluent. The active materials can be administered by any appropriate route, for example, orally, parenterally, intravenously, intradermally, subcutaneously, or topically, in liquid, cream, gel, or solid form, or by aerosol form.

As used herein, the term pharmaceutically acceptable salts or complexes refers to salts or complexes that retain the desired biological activity of the above-identified compounds and exhibit minimal undesired toxicological effects. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucose/mine, tetraethylammonium, or ethylenediamine; or (c) combinations of (a) and (b); e.g., a zinc tannate salt or the like. The compounds can also be administered as pharmaceutically acceptable quaternary salts known by those skilled in the art, which specifically include the quaternary ammonium salt of the formula —NR$^+$Z$^-$, wherein R is alkyl or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 10 ng/kg to 300 mg/kg, preferably 0.1 to 100 mg/kg per day, more generally 0.5 to about 25 mg per kilogram body weight of the recipient per day. A preferred dosage for cardiovascular indications is in the range 10 ng/kg to 20 mg/kg. A typical topical dosage will range from 0.01–3% wt/wt in a suitable carrier. The effective dosage range of the. pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The compound is conveniently administered in any suitable unit dosage form, including but not limited to one containing 1 to 3000 mg, preferably 5 to 500 mg of active ingredient per unit dosage form. A oral dosage of 25–250 mg is usually convenient.

The active ingredient is preferably administered to achieve peak plasma concentrations of the active compound of about 0.00001–30 mM, preferably about 0.1–30 µM.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the-scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterores; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable derivatives or salts thereof can also be mixed with other active materials that do not impair the desired action, or with materials that supplement the desired action, such as antibiotics, antifungals, other antiinflammatories, or antiviral compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation (CA) and Scios Nova (Baltimore, Md.).

Liposomai suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

III. Biological Activity

A wide variety of biological assays have also been used to evaluate the ability of a compound to inhibit the enzyme 5-lipoxygenase. For example, a cytosol 5-lipoxygenase of rat basophilic leukemia cells (RBL) has been widely utilized in studies on leukotriene biosynthesis. Compounds that inhibit 5-lipoxygenase decrease the levels of leukotrienes.

Another biological assay used to evaluate the ability of a compound to inhibit the enzyme 5-lipoxygenase is based on the classic pharmacological model of inflammation induced by inhibition of $LTB_4$ from ionophore stimulated human whole blood.

Any of these assays, or other assays known to those skilled in the art, can be used to evaluate the activity of the compounds disclosed herein. Examples of these evaluations are provided below.

EXAMPLE 2

Effect of Compounds on Cytosol 5-Lipoxygenase of Rat Basophile Leukemia Cells

RBL-2H3 cells were grown to confluence in tissue culture flasks according to Carter et al. (J PharmExp Ther 256(3); 929–937, 1991). The cells were harvested and washed five times in calcium-and magnesium-free D-PBS. The cells were suspended at $2 \times 10^7$/ml in 10 mM BES, 10 mM PIPES, pH 6.8, 1 mM EDTA, and then sonicated. The sonicate was centrifuged at 20,000×g for 20 minutes at 4° C. The supernatant was then removed and stored in aliquots at −70° C.

The 5-LO activity in the RBL-2H3 preparation was determined as follows: 0.1 ml reactions consisting of 0.7 mM $CaCl_2$, 100 mM NaCl, 1 mM EDTA, 10 mM BES, 10 MM PIPES, pH 7.4, varying concentrations of test compound dissolved in DMSO (7.5% DMSO final in assay), and an amount of the RBL-2H3 preparation that will convert 15% of the arachidonic acid substrate mixture to oxygenated products (determined experimentally for each RBL-2H3 preparation), were incubated for 20 minutes at room temperature. The reaction was initiated by the addition of 5 ul of the arachidonic acid substrate mixture (0.944 nmol [$^{14}C$] arachidonic acid and 6.06 nmol arachidonic acid per assay in 0.028% $NH_4OH$), and allowed to proceed for 5 minutes at 37° C. The reaction was terminated by the addition of 0.12 ml of a mixture of (i) 1.66 mg/ml triphenylphosphine in ethyl ether; (ii) methanol; and (iii) 0.2M citric acid (30:4:1); followed by centrifugation at 1000×g for 1 minute. 50 ul of the organic phase was drawn into a glass capillary piper and spotted onto silica gel 60A TLC plates (Whatman #6KDF). The plates were developed in ethyl ether acetic acid (100:0.1) for 25 minutes at room temperature. The plates were exposed to Kodak X-OMAT AR film for 40 hours. The film was developed, scanned using a densitometer, and the peak areas of arachidonic acid and its product(s) are calculated. The percent inhibition was determined from the amount of [14C]-arachidonic acid converted into oxygenated products in samples containing test compound relative to that of control samples (no test compound).

The results are provided in Table 1.

EXAMPLE 3

Inhibition of Leukotriene $B_4$ Production in Ionophore-stimulated human whole blood Human blood was drawn into heparinized blood collection tubes, and aliquoted in 1 ml portions into 1.5 ml microfuge tubes. Test compound (5 ml) of varying concentrations, dissolved in DMSO, was added to the blood sample and incubated for 15 minutes at 37° C. Calcium ionophore (5 ml, A23187) in DMSO was added to a final concentration of 50 mM, and the samples were incubated for 30 minutes at 37° C. Samples are then centrifuged at 1100×g (2500 rpm, H1000B rotor, in a Sorvall centrifuge) for 10 minutes at 4° C. Supernatant (100 ml) was transferred into a 1.5 ml microfuge tube, 400 ml of cold methanol added, and proteins precipitated on ice for 30 minutes. The samples were centrifuged at 110×g for 10 minutes at 4° C., and the supernatant assayed for $LTB_4$ using a commercially available EIA kit (Cayman Chemical) according to manufacturer's specifications.

The results are provided in Table 2.

TABLE 2

| Compound | RBL IC50 nM | HWB IC50 μm | ex vivo LTB4 dose mg/k | % inh. | time minutes |
|---|---|---|---|---|---|
| Compound 2 (4-F-phenyl-O-CH2-[tetrahydrofuran S,R]-(CH2)4-N(OH)-C(O)-NH2) | 1230 1400 | 0.153 | 3,iv 3,iv 3,iv | MOUSE 89 22 36 | 15 60 180 |
| | | | 2,po 5,po | RAT 34 34 | 900 900 |
| Compound 1 (4-F-phenyl-O-CH2-[tetrahydrofuran S,S]-C≡C-CH2CH2-N(OH)-C(O)-NH2) | 1380 1490 560 1600 720 | 0.094 0.27 0.078 | 3,iv 3,iv 3,iv | MOUSE 94 86 44 | 15 60 180 |
| | | | 5,po 2,po 2,po | RAT 29 93 5 | 900 60 360 |
| Compound 3 (4-F-phenyl-O-CH2-[tetrahydrofuran S,R CIS]-C≡C-CH2CH2-N(OH)-C(O)-NH2) | 2000 1260 1560 880 | 0.43 0.52 | 2,po 2,po | RAT 86 63 | 60 360 |
| Compound 4 (4-F-phenyl-O-CH2-[tetrahydrofuran R,R TRANS]-C≡C-CH2CH2-N(OH)-C(O)-NH2) | 1350 1380 | 0.15 0.27 | | | |
| Compound 5 (4-F-phenyl-O-CH2-[tetrahydrofuran R,TRANS]-S-(CH2)4-N(OH)-C(O)-NH2) | 950 | 0.42 | | | |
| Compound 6 (4-F-phenyl-O-CH2-[tetrahydrofuran R,S CIS]-C≡C-CH2CH2-N(OH)-C(O)-NH2) | 910 | 0.18 | | | |

EXAMPLE 4

Ex-vivo mouse whole blood 5-lipoxygenase evaluation

CD-1 female mice, weighing 18–25 grams, and CD female rats, weighing 150–230 grams, were obtained from Charles River Labs. Test compounds were dissolved in 0.5% DMSO in 0.9% NaCl for administration in mice (0.5 mg/ml) and in an alcohol vehicle (2% benzyl alcohol, 1% ethanol, 40% PEG 300, 10% propylene glycol, 47% of 5% dextrose and 3.5% pluronic F-68 in DiH$_2$O) for use in rats (5 mg/ml). Animals were injected with compounds (5 mg/kg) or corresponding vehicle (0.5% DMSO in saline, 10 ml/kg for mice; alcohol vehicle, 1 ml/kg for rats) 15 minutes before they were sacrificed by decapitation. Heparinized whole blood (0.3 ml) was added into 1.5 ml Eppendorf centrifuge tube containing 3 ml of 2 mM calcium ionophore A23187 (the final concentration of A23187 was 20 mM). The sample was incubated for 30 minutes in a water bath at 37° C., and then centrifuged for 2 minutes. The plasma was diluted (×120) and assayed for LTB$_4$ using EIA.

The results are provided in Table 2

EXAMPLE 5

Glucuronidation Studies

Figure 2:
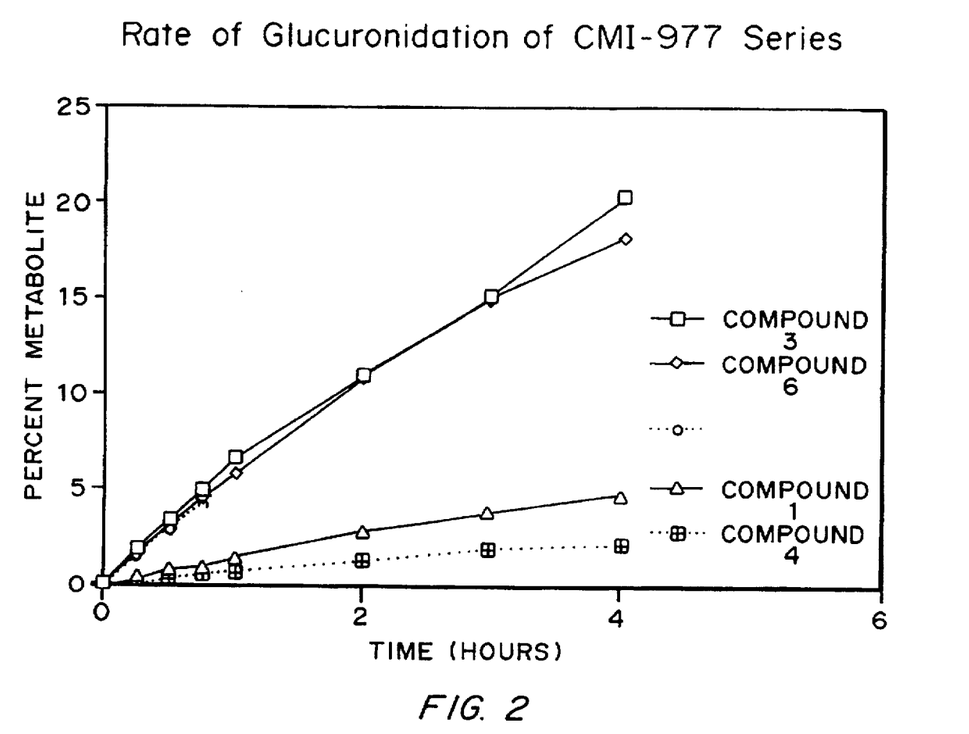
FIG. 2 is a graph of the rate of glucuronidation of compounds 1, 3, 4, and 6 (as illustrated in Table 2) as measured in percent metabolite versus time (hours).

The rate of glucuronidation is a measure of the metabolic stability in vivo of the compounds disclosed herein. In vitro glucuronidation reactions were carried out with reaction mixtures containing 2 mg/ml of human microsomal protein, 5 mM magnesium chloride, 100 mM Tris HCl (pH=7.4), 0.1–1.0 mM substrate and 3 mM UDP-glucuronic acid. After incubation at 37° C. for 0 (control), 15, 30, 45, 60, 90, 120, 180, and 240 minutes, 40 μl aliquots of the reaction mixture were mixed with 80 μl of acetonitrile and centrifuged to remove the precipitated protein. Aliquots of the supernatant were analyzed by reverse phase HPLC to determine the disappearance of parent compounds and formation of metabolites. The results are provided in FIG. 2.

EXAMPLE 6

Eosinophil infiltration Assay

Accumulation of inflammatory cells in the lung is one of the pathological features of asthma. Elevation of leukocytes, particularly of eosinophils, in blood and lung lavage fluid has been observed after allergen inhalation in the patients. Eosinophils appear to be important effector cells in allergic inflammation, with the cytotoxic properties of its granule proteins and the potential of releasing inflammatory mediators. Prevention of allergen-induced eosinophil influx into the lung is considered a credible target for novel anti-asthmatic drugs.

Leukotrienes are products of the arachidonic acid 5-lipoxygenase (5-LO) pathway. Lipoxygenase metabolites (LTB4, 5-oxo-15-hydroxy-eicosatetraenoic acid) have been identified that possess potent activity to recruit eosinophils. A 5-LO inhibitor which is able to block immediate bronchoconstriction and also to reduce later accumulation of eosinophils into lung tissue consequent to allergen challenge may be beneficial to the prevention and treatment of asthma.

Eosinophil infiltration into the lung can be measured by counting the cell number in the bronchoalveolar lavage fluid (BALF) from allergen-challenged mice.

Mice model: Male $C_{57}$ BL/6 mice, weighing 21–23 g, were actively sensitized to OVA by administering 10 μg OVA and 1 mg $Al(OH)_3$ in 0.2 ml 0.9% NaCl on Day 1. Hypersensitivity was developed following a daily inhalation of aerosolized 1% OVA or saline for 30 minutes on Day 14 to Day 21. The compounds were prepared in a 10% PEG 200 or 0.5% carboxymethylcellulose and administered at 20 mg/kg orally, b.i.d. on Day 18 to Day 22. Animals were bled from the carotid under anesthesia four hours after the last inhalation of OVA. BAL was performed with 2×1 ml DPBS (w/o 4 $C_8^{2+}$, $M_g^{2+}$) containing 0.5 mM sodium EDTA at 37° C. via a tracheal cannulation. The total cells in BAL fluid were counted by a Sysmex microcelcounter (F-800). The differential cells in BAL fluid were counted by a Sysmex microcellcounter (F-800). The differential cells were counted on a cytospin preparation and white giemsa stain. % of Inhibition on total cell or Eosinophil accumulation= [(vehicle-sham)−(treated-sham)]/(vehicle-sham)×100. (See Yeadon M. et al. Agents Actions 38:8–17, 1993; Brusselle G. G. et al. ALA'94, A754; Schwenk U. et al. J. Biol. Biochem. 267:12482–12488, 1992; and Clinic M. et al. Cur. Opin. Immunol. 6:860–864, 1994).

Modifications and variations of the present invention relating to compounds that reduce the formation of oxygen radicals during an inflammatory or immune response will be obvious to those skilled in the art from the foregoing detailed description of the invention. Such modifications and variations are intended to come within the scope of the appended claims.

We claim:
1. A compound of formula:

wherein:

Ar is an aryl or heteroaryl group that is optionally substituted with halo, lower alkoxy, lower aryloxy, W, cyano, or $R^3$;

m is 0 or 1;

n is 1–6;

W is independently —AN(OM)C(O)N($R^3$)$R^4$, —N(OM)C(O)N($R^3$)$R^4$, —AN($R^3$)C(O)N(OM)$R^4$, —N($R^3$)C(O)N(OM)$R^4$, —AN(OM)C(O)$R^4$, —N(OM)C(O)$R^4$—, AC(O)N(OM)$R^4$, —C(O)N(OM)$R^4$, —C(O)NHA;

A is lower alkylene, lower alkenylene, lower alkynylene, alkylarylene or aryl alkylene, or a hetero derivative thereof, wherein one or more carbons optionally can be replaced by O, N, or S (with valence completed with hydrogen or oxygen as necessary), however, —Y—A—, —A—, and —AW— must not include two adjacent heteroatoms;

M is hydrogen, a pharmaceutically acceptable cation, or a metabolically cleavable leaving group;

X is O, S, S(O), S(O)$_2$, NR$^3$, or CHR$^5$;

Y is O, S, S(O), S(O)$_2$, NR$^3$, or CHR$^5$;

Z is O, S, S(O), S(O)$_2$, NR$^3$;

$R^1$ and $R^2$ are independently hydrogen, lower alkyl, cyclopropylmethyl, ethyl, isopropyl, butyl, pentyl hexyl, and $C_{3-8}$ cycloalkyl, for example, cyclopentyl; halo lower alkyl, halo; or —COOH;

$R^3$ and $R^4$ are independently hydrogen or alkyl, alkenyl, alkynyl, aryl, arylalkyl, alkylaryl, $C_{1-6}$ alkoxy-$C_{1-10}$ alkyl, $C_{1-6}$ alkylthio-$C_{1-10}$ alkyl, heteroaryl, or heteroarylalkyl-;

$R^5$ is hydrogen, lower alkyl, lower alkenyl, lower alkynyl, arylalkyl, alkylaryl, —AN(OM)C(O)N($R^3$)$R^4$, —AN($R^3$)C(O)N(OM)$R^4$, —AN(OM)C(O)$R^4$, —AC(O)N(OM)$R^4$, —AS(O)x$R^3$, —AS(O)$_x$H$_2$C(O)$R^3$, —AS(O) xCH$_2$CH(OH)$R^3$, or —AC(O)NHR$^3$;

wherein x is 0–2.

2. The compound of claim 1, wherein Ar is selected from the group consisting of phenyl, trimethoxyphenyl, dimethoxyphenyl, fluorophenyl, difluorophenyl, pyridyl, dimethoxypyridyl, quinolinyl, furyl, imidazolyl, and thienyl.

3. The compound of claim 1, wherein Ar is 4-fluorophenyl.

4. The compound of claim 1, wherein Z is O.

5. The compound of claim 1, wherein Z is S.

6. The compound of claim 1, wherein —(Y)$_m$W is selected from the group consisting of:

-continued

7. The compound of claim 1, wherein —(Y)$_m$W is selected from the group consisting of:

8. The compound of claim 1, 2, 3, 4, 5, 6, or 7 in at least 97% enantiomerically enriched form.

9. A compound selected from the group consisting of 2S,5S-trans-2-(4-fluorophenoxymethyl)-5-(4-protectedoxy-1-butynyl)tetrahydrofuran and 2S,5R-cis-2-(4-fluorophenoxymethly)-5-(4-protectedoxy-1-butynyl) tetrahydrofuran.

10. The compound of claim 1 that is 2S,5-trans-2-(4-fluorophenoxymethyl)-5-(4-N-hydroxyureidyl-1-butyl) tetrahydrofuran.

11. The compound of claim 1 that is 2S,5S-trans-2-(4-fluorophenoxymethyl)-5-(4-N-hydroxyureidyl-1-butynyl) tetrahydrofuran.

12. The compound of claim 1 that is 2R,5S-trans-2-(4-fluorophenoxymethyl)-5-(4-N-hydroxyureidyl-1-butyl) tetrahydrofuran.

13. The compound of claim 1 that is 2R,5R-trans-2-(4-fluorophenoxymethyl)-5-(4-N-hydroxyureidyl-1-butynyl) tetrahydrofuran.

14. A pharmaceutical composition comprising an effective antiinflammatory amount of the compound of claim 1 or a pharmaceutically acceptable salt thereof, in combination with a pharmaceutically acceptable carrier.

15. The pharmaceutical composition of claim 14 that an effective antiinflammatory mount of the compound of claim 10 or a pharmaceutically acceptable salt thereof, in combination with a pharmaceutically acceptable carrier.

16. The pharmaceutical composition of claim 14 that an effective antiinflammatory amount of the compound of claim 11 or a pharmaceutically acceptable salt thereof, in combination with a pharmaceutically acceptable carrier.

17. The pharmaceutical composition of claim 14 that an effective antiinflammatory amount of the compound of claim 12 or a pharmaceutically acceptable salt thereof, in combination with a pharmaceutically acceptable carrier.

18. The pharmaceutical composition of claim 14 that an effective antiinflammatory mount of the compound of claim 13 or a pharmaceutically acceptable salt thereof, in combination with a pharmaceutically acceptable carrier.

19. The pharmaceutical composition of claim 14 that an effective antiinflammatory mount of the compound of claim 2 or a pharmaceutically acceptable salt thereof, in combination with a pharmaceutically acceptable carrier.

20. The pharmaceutical composition of claim 14 that an effective antiinflammatory amount of the compound of claim 3 or a pharmaceutically acceptable salt thereof, in combination with a pharmaceutically acceptable carrier.

21. The pharmaceutical composition of claim 14 that an effective antiinflammatory mount of the compound of claim 6 or a pharmaceutically acceptable salt thereof, in combination with a pharmaceutically acceptable carrier.

22. The pharmaceutical composition of claim 14 that an effective antiinflammatory amount of the compound of claim 7 or a pharmaceutically acceptable salt thereof, in combination with a pharmaceutically acceptable carrier.

* * * * *